(12) United States Patent
Onodera et al.

(10) Patent No.: US 7,930,940 B2
(45) Date of Patent: Apr. 26, 2011

(54) ULTRASONIC TRANSDUCER

(75) Inventors: Akira Onodera, Shiga (JP); Yasunori Aoyama, Shiga (JP)

(73) Assignee: Toray Engineering Co., Ltd., Tokyo (JP)

( * ) Notice: Subject to any disclaimer, the term of this patent is extended or adjusted under 35 U.S.C. 154(b) by 569 days.

(21) Appl. No.: 12/007,767

(22) Filed: Jan. 15, 2008

(65) Prior Publication Data
US 2008/0282805 A1  Nov. 20, 2008

(30) Foreign Application Priority Data

Jan. 30, 2007 (JP) ................................ 2007-019872

(51) Int. Cl.
*G01N 29/00* (2006.01)

(52) U.S. Cl. ............... 73/629; 73/579; 73/597; 73/632; 73/644

(58) Field of Classification Search .................... 73/579, 73/597, 598, 600, 629, 632, 644; 439/76.2, 439/67
See application file for complete search history.

(56) References Cited

U.S. PATENT DOCUMENTS

| | | | | |
|---|---|---|---|---|
| 4,408,113 A | * | 10/1983 | Inoue | 219/69.17 |
| 4,870,982 A | * | 10/1989 | Liu | 134/135 |
| 5,099,693 A | * | 3/1992 | Payne et al. | 73/632 |
| 5,684,252 A | * | 11/1997 | Kessler et al. | 73/618 |
| 5,698,787 A | * | 12/1997 | Parzuchowski et al. | 73/643 |
| 6,355,498 B1 | * | 3/2002 | Chan et al. | 438/48 |
| 6,501,016 B1 | * | 12/2002 | Sosnowski | 174/382 |
| 6,655,967 B2 | * | 12/2003 | Oda | 439/76.2 |
| 7,188,526 B2 | * | 3/2007 | Taylor et al. | 73/618 |
| 7,473,107 B2 | * | 1/2009 | Ice | 439/79 |

FOREIGN PATENT DOCUMENTS

| | | |
|---|---|---|
| JP | 4-132498 A | 5/1992 |
| JP | 6-80169 U | 11/1994 |

* cited by examiner

*Primary Examiner* — J M Saint Surin
(74) *Attorney, Agent, or Firm* — Smith Patent Office (57) ABSTRACT

An ultrasonic transducer incorporated into an ultrasonic inspection apparatus for examining existence of defect in a sample dipped in water comprises a transducer main part having an oscillator which projects an ultrasonic wave to the sample, receives the reflected wave from the sample and outputs the received reflected wave as an echo signal, a transmitter substrate producing a drive pulse for emitting the ultrasonic wave to the oscillator, a receiver substrate for amplifying the echo signal, a housing for containing therein both substrates electrically connected, and connecting member for electrically connecting between a signal input/output terminal and the side of the oscillator in the transducer main part, wherein, when a maximum operational frequency of the ultrasonic wave emitted from the oscillator is referred to as fmax [MHz], the connecting member is set at a length of 100/fmax [cm] or less. Even if the sample to be examined is small, a desirable defect inspection can be achieved at an excellent examination accuracy.

7 Claims, 11 Drawing Sheets

ULTRASONIC TRANSDUCER

BACKGROUND OF THE INVENTION

1. Field of the Invention

The present invention relates to an ultrasonic transducer. More specifically, the present invention relates to an ultrasonic transducer which is a device functioning as a source for projecting an ultrasonic wave to a sample to be examined and functioning as a source for receiving a wave reflected from the sample.

2. Description of the Background Art

Figure 12:
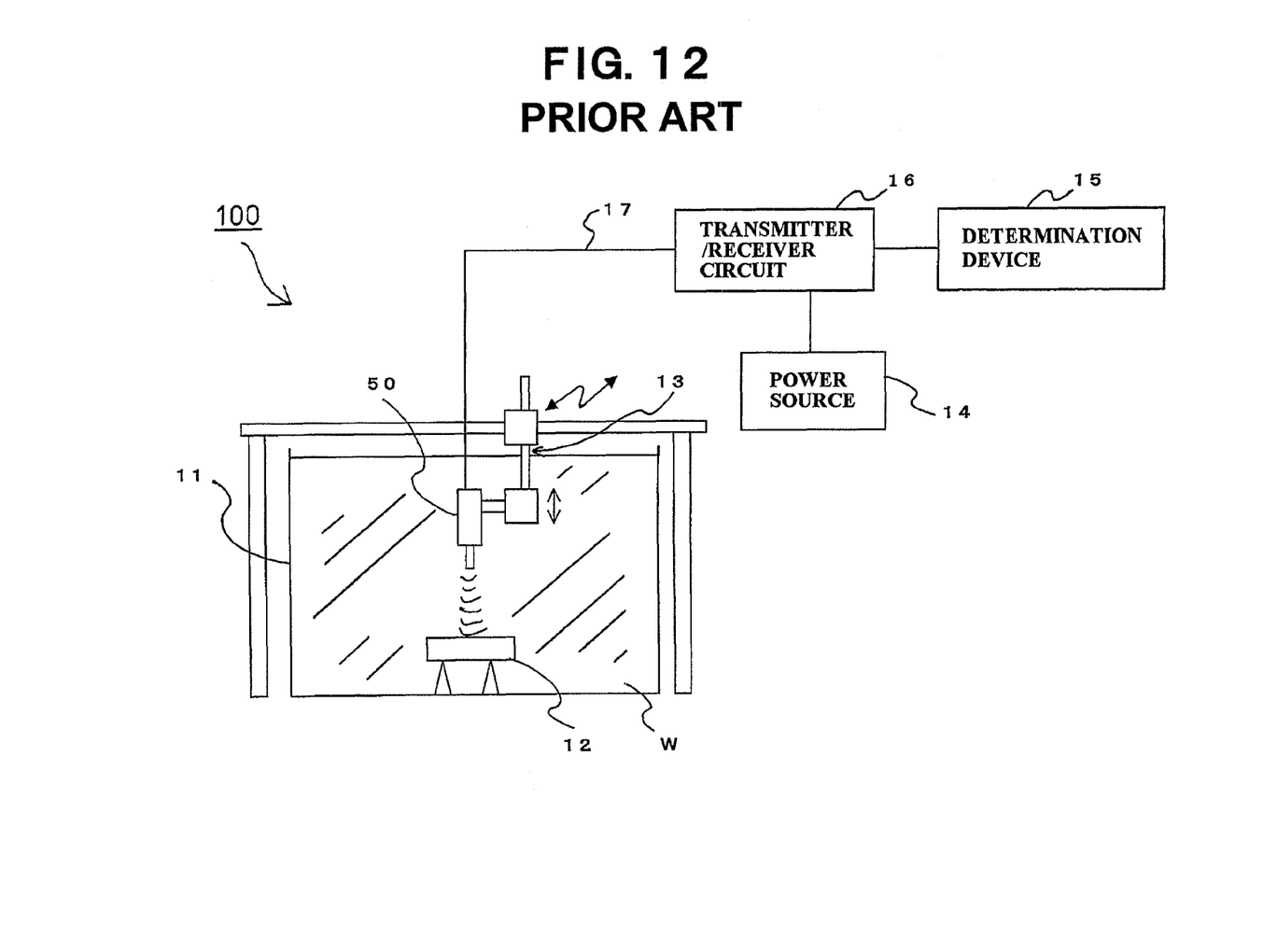
FIG. 12 is a schematic diagram showing an example of a conventional ultrasonic inspection apparatus.

An ultrasonic inspection apparatus is known as an apparatus which projects an ultrasonic wave to a sample to be examined, dipped in water, through the water, receives a reflected wave from the sample and detects a defect such as a break away or a flaw in the sample based on a wave form of an echo signal of the reflected wave (for example, Japanese Utility Model Laid-Open 6-80169), FIG. 12 shows an example of a conventional ultrasonic inspection apparatus. As shown in FIG. 12, the conventional ultrasonic inspection apparatus 100 comprises a water bath 11 filled with water W, a sample to be examined 12 provided to be dipped in water bath 11, an ultrasonic transducer 50 functioning as a source for projecting an ultrasonic wave to the sample to be examined 12 and functioning as a source for receiving a reflected wave from the sample 12, a transmitter/receiver circuit 16 sending a drive pulse to the ultrasonic transducer 50 and amplifying an echo signal received, an electric connecting cord 17 for electrically connecting between the ultrasonic transducer 50 and the transmitter/receiver circuit 16, a scanning device 13 for moving the ultrasonic transducer 50 in horizontal and vertical directions, a power source 14 for supplying power to the respective parts, and a determination device 15 for determining existence of defect in the sample 12 based on the wave form of the echo signal outputted from the transmitter/receiver circuit 16.

The ultrasonic wave projected from ultrasonic transducer 50 has a high-frequency component of from about 10 MHz to about 200 MHz. Further, the electric signal outputted from ultrasonic transducer 50 after receiving the reflected wave is a signal having a very low voltage of about several mV.

In such a conventional apparatus, the length of the electric connecting cord 17 for electrically connecting between the ultrasonic transducer 50 and the transmitter/receiver circuit 16 was several-tens cm at shortest, and in a case of a long cord, it was several meters. If the electric connecting cord 17 is thus long, when a drive pulse is sent from the transmitter/receiver circuit 16 to the ultrasonic transducer 50, there is a case where the drive pulse is attenuated and weakened. Similarly, when an echo signal is sent from the ultrasonic transducer 50 to the transmitter/receiver circuit 16, there is a case where the high-frequency component of the echo signal is attenuated and weakened. As a result, there occurs a problem that the examination accuracy may deteriorate. Recently, miniaturization of electronic parts is proceeded, and when such electronic parts are employed as the samples to be examined 12, it is an important subject to be able to detect very fine defects. Therefore, it is important to be able to send and receive high-frequency wave components having a high resolution without weakening.

SUMMARY OF THE INVENTION

Accordingly, it is an object of the present invention to provide an ultrasonic transducer incorporated into an ultrasonic inspection apparatus, which can detect a defect at an excellent examination accuracy even for a small sample to be examined.

To achieve the foregoing and other objects, an ultrasonic transducer according to the present invention is incorporated into and used for an ultrasonic inspection apparatus, which projects an ultrasonic wave to a sample to be examined, dipped in water, through the water, receives a reflected wave from the sample and detects a defect such as a break away or a flaw in the sample based on a wave form of an echo signal of the reflected wave. The ultrasonic transducer comprises a transducer main part having an oscillator which emits the ultrasonic wave in accordance with a drive pulse, receives the reflected wave from the sample and outputs the received reflected wave as the echo signal; a transmitter substrate provided for producing the drive pulse which gives an energy for emitting the ultrasonic wave to the oscillator in the transducer main part; a receiver substrate provided for amplifying the echo signal received by the oscillator in the transducer main part; a housing formed as a cylindrical shape for containing a transmitter/receiver circuit substrate assembly (assembly of circuit substrates for sending and receiving wave signals) which is formed by electrically connecting the transmitter substrate and the receiver substrate at a form confronted with each other and at a condition free to be attached and detached; and connecting means for electrically connecting between a signal input/output terminal means, provided on the transmitter substrate and functioning as an output terminal for outputting the drive pulse to the oscillator as well as functioning as an input terminal for inputting the echo signal outputted from the oscillator, and the oscillator in the transducer main part. In this ultrasonic transducer, when a maximum operational frequency of the ultrasonic wave emitted from the oscillator is referred to as fmax [MHz], the connecting means is set at a length of 100/fmax [cm] or less.

In the above-described ultrasonic transducer, the transducer main part and the transmitter/receiver circuit substrate assembly may be integrated with each other. Further, the signal input/output terminal means and the oscillator may be electrically connected via a solder. Alternatively, the signal input/output terminal means and the oscillator may be electrically connected via a lead wire. Moreover, the signal input/output terminal means and the oscillator may be electrically connected via a connector which is free to be connected and disconnected. This connector can be employed even in a case using the above-described solder or lead wire. Further, the signal input/output terminal means and the oscillator may be electrically connected via a matched circuit substrate. Furthermore, because the transmitter substrate and the receiver substrate are disposed in the housing at a relatively close condition, in order to prevent the receiver substrate from picking up a noise, an electromagnetic wave shielding means may be interposed between the transmitter substrate and the receiver substrate.

In the present invention, the oscillator provided in the transducer main part and the signal input/output terminal means provided on the transmitter/receiver circuit substrate assembly are electrically connected to each other by the connecting means. This connecting means is formed at a length of 100/fmax [cm] or less when the maximum operational frequency of the ultrasonic wave emitted from the oscillator is referred to as fmax [MHz].

The reason will be explained why the upper limit of the length of the connecting means is set at 100/fmax [cm] as described above. Because the impedance of the connecting means becomes greater as the operational frequency of the ultrasonic wave is higher, in order to prevent weakening of signal, the upper limit length of the connecting means must be a length inversely proportional to the maximum operational frequency. The reason why 100/fmax [cm] is adequate is based on the actually determined data (FIG. 6) of the frequency property in the embodiment described later. In the present invention, when the maximum operational frequency is relatively high, for example, such as 200 MHz, it is necessary to set the upper limit of the length of the connecting means at 100/200=0.5 [cm]. On the contrary, when the maximum operational frequency is relatively low, for example, such as 50 MHz, the upper limit of the length of the connecting means may be set at 100/50=4 [cm].

In the present invention, because the length of the connecting means is set at the upper limit, adequately decided in accordance with the maximum operational frequency, or less, when the drive pulse is sent from the signal input/output terminal means to the transducer main part, very rarely occurs a case where the drive pulse is attenuated and weakened. Similarly, when the echo signal is sent from the transducer main part to the signal input/output terminal means, very rarely occurs a case where the high-frequency component of the echo signal is attenuated and weakened. Consequently, even in a case where the sample to be examined is small, the defect examination can be carried out at an excellent examination accuracy.

Thus, in the ultrasonic transducer according to the present invention, even when a sample to be examined is small, a defect in the sample can be detected at an excellent examination accuracy.

Further objects, features, and advantages of the present invention will be understood from the following detailed description of preferred embodiments of the present invention with reference to the accompanying figures.

BRIEF DESCRIPTION OF THE DRAWINGS

Embodiments of the invention are now described with reference to the accompanying figures, which are given by way of example only, and are not intended to limit the present invention.

EXPLANATION OF SYMBOLS

1: ultrasonic transducer
2: transducer main part
3: signal transmitter/receiver part
4: housing
5: transmitter/receiver circuit substrate assembly
6: cable for power source
7: cable with connector
8: resin mold
10: ultrasonic inspection apparatus
11: water bath
12: sample to be examined
13: scanning device
14: power source
15: determination device
24: oscillator
51: transmitter substrate
51a, 51b: signal input/output terminal
52: receiver substrate
53a, 53b: solder (connecting means)
54a, 54b: lead wire (connecting means)
55, 56: connector
57: matched circuit substrate
61a, 61b: shield case
S2: drive pulse
S3: echo signal
S5: ultrasonic wave
W: water

DETAILED DESCRIPTION OF PREFERRED EMBODIMENTS

Figure 1:
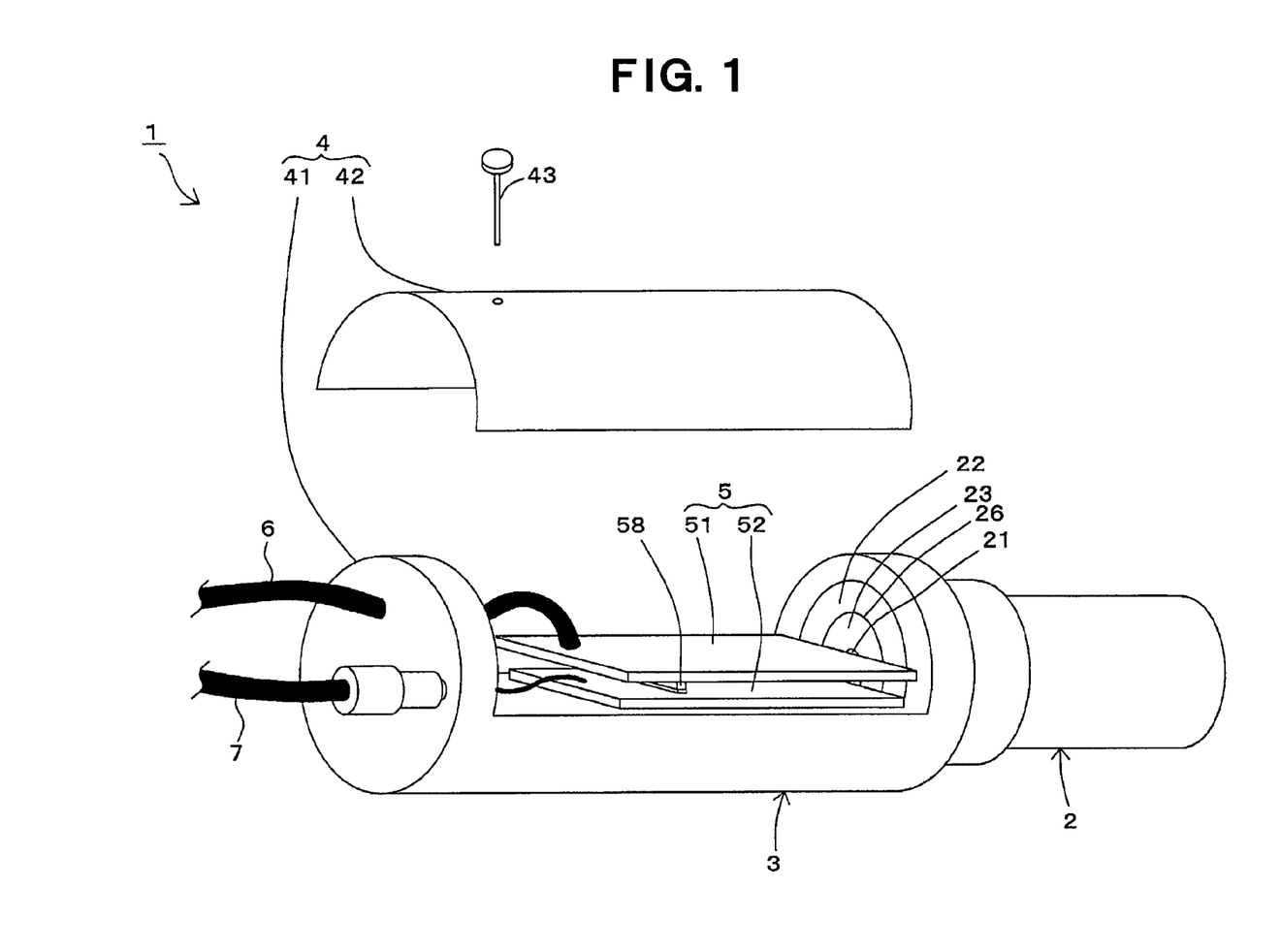
FIG. 1 is a schematic exploded perspective view of an ultrasonic transducer according to the present invention.
Figure 2:
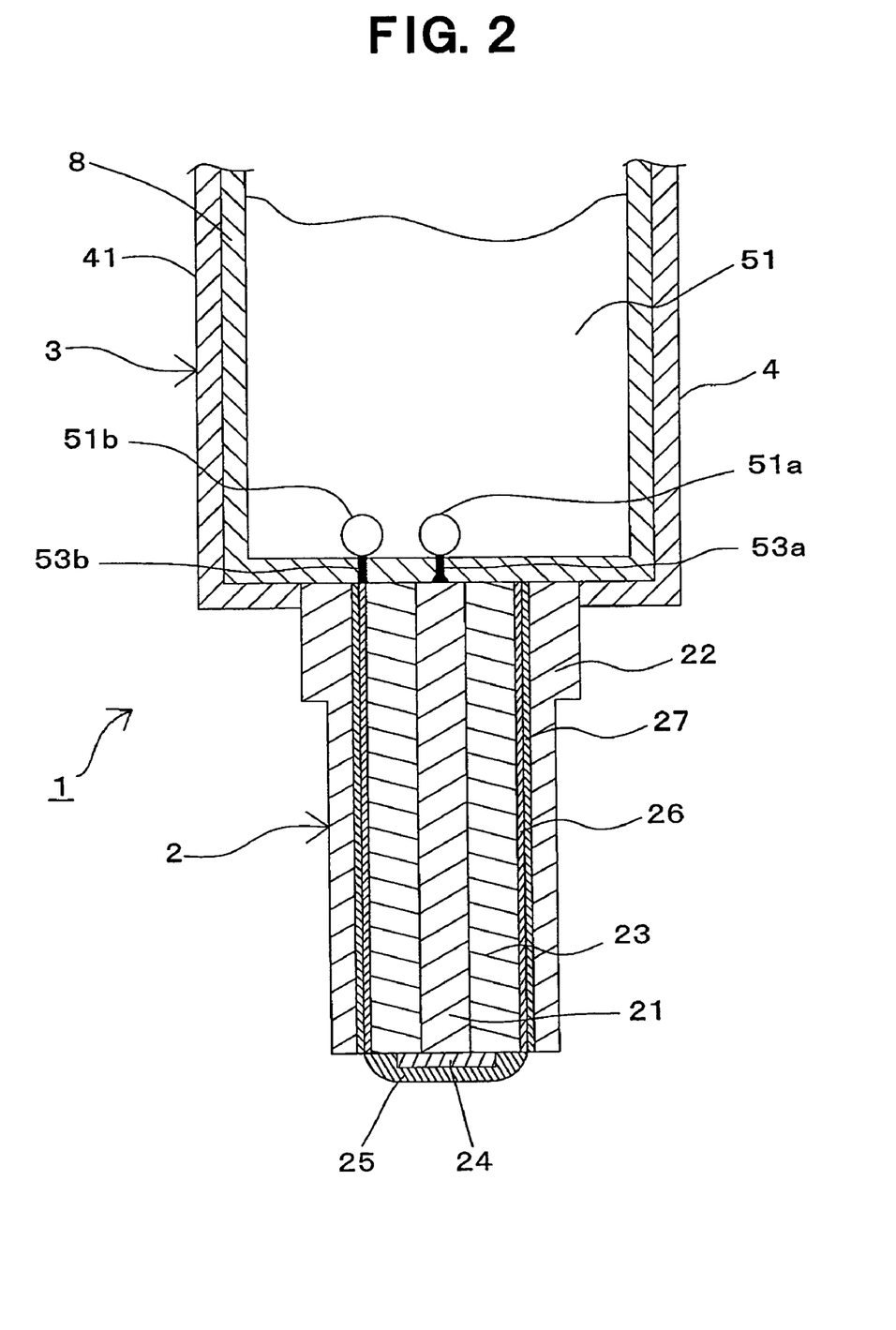
FIG. 2 is a sectional view of a part of an ultrasonic transducer according to a first embodiment of the present invention.

FIG. 1 shows a schematic structure of an ultrasonic transducer according to the present invention, and FIG. 2 shows a main part of an ultrasonic transducer according to a first embodiment of the present invention. As shown in FIG. 1, an ultrasonic transducer 1 according to the present invention has a transducer main part 2 and a signal transmitter/receiver part 3 (part for sending and receiving signals).

As shown in FIG. 2, transducer main part 2 has an anode 21, a side wall part 22, an insulation member 23, an oscillator 24 and a cathode 25, and the transducer main part 2 is integrated with signal transmitter/receiver part 3 at a state where the oscillator 24 is located at a position opposite to the position of the signal transmitter/receiver part 3.

Anode 21 is made from a brass and formed in a columnar shape. Side wall part 22 is made from a stainless steel and formed in a schematic cylindrical shape having a diameter into which anode 21 can be inserted. Insulation member 23 is made from polybutylene terephthalate (PBT) and provided so as to fill the space between the outer circumferential surface of anode 21 and the inner circumferential surface of side wall part 22. Oscillator 24 is made from polyvinylidene fluoride/ trifluoro ethylene (PVDF/TrFE) and formed in a film shape having a thickness of from about 3 μm to about 60 μm so as to be positioned on one end surface of anode 21.

Cathode 25 is made from gold and formed in a film shape having a thickness of from about 0.1 μm to about 0.2 μm so as to cover the surface of oscillator 24. A copper foil 26 is provided at a film shape around the outer circumferential surface of insulation member 23, and this copper foil 26 is conducted to cathode 25. By interposing insulation member 23 between copper foil 26 and anode 21, a capacitor with a dielectric made of the insulation member 23 is formed. Where, an insulation tape 27 is interposed for insulating between copper foil 26 and side wall part 22.

In FIG. 1, signal transmitter/receiver part 3 has a housing 4 and a transmitter/receiver circuit substrate assembly 5. Housing 4 is made from a stainless steel and formed in a schematic cylindrical shape. The housing 4 comprises a housing main part 41 and a housing cover 42. The housing cover 42 is attached to housing main part 41 via a screw 43, free to be attached/detached. To the end surface of housing 4 opposite to the side provided with transducer main part 2, attached are a cable for power source 6 for supplying the drive power to transmitter/receiver circuit substrate assembly 5 and a cable with connector 7 for taking out RF (reference) signal S4 from transmitter/receiver circuit substrate assembly 5 to outside.

Transceiver circuit board assembly 5 comprises a transmitter substrate 51 and a receiver substrate 52. These two substrates 51 and 52 are fixed to housing main part 41 by an attachment member such as a bracket so as to confront with each other in housing 4.

Figure 5:
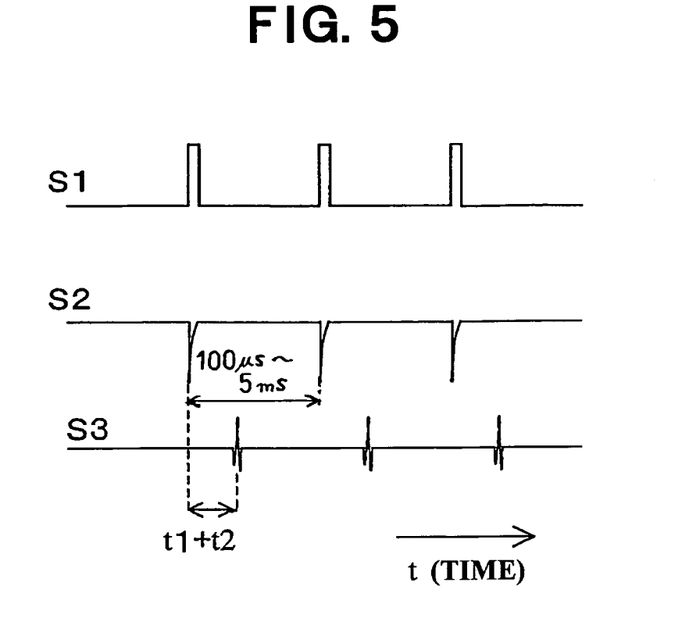
FIG. 5 is a time chart showing output timings of a trigger signal, a drive pulse and an echo signal.

Transmitter substrate 51 is a substrate of circuit structured so as to produce a drive pulse S2. Drive pulse S2 gives an energy to oscillator 24 for emitting an ultrasonic wave S5 in transducer main part 2. More concretely, this transmitter substrate 51 is constructed so that drive pulse S2 is outputted at a constant period by discharging the electric charge stored in the capacitor at a timing determined by providing a trigger signal S1. The value of this constant period is selected from the range of 100 μs to 5 ms as shown in FIG. 5. Oscillator 24 emits ultrasonic wave S5 by the drive pulse S2 with the constant period, which is produced by the discharge from the capacitor. The frequency component of the ultrasonic wave S5 emitted from oscillator 24 can be designed by the thickness of oscillator 24, etc.

Receiver substrate 52 is a substrate of circuit structured so as to amplify the echo signal S3 received by oscillator 24 in transducer main part 2. Concretely, it has an appropriate amplifying circuit such as an operational amplifier. Transmitter substrate 51 and receiver substrate 52 are electrically connected to each other by a connector 58 at a condition free to be attached and detached.

As shown in FIG. 2, transmitter substrate 51 has signal input/output terminals 51a and 51b. Signal input/output terminals 51a and 51b function as an output terminal for outputting drive pulse S2 to transducer main part 2 and an input terminal for inputting echo signal S3 outputted from transducer main part 2.

The electrical connection between a signal input/output terminal 51a for transmitter substrate 51 and anode 21 in transducer main part 2, and the electrical connection between a signal input/output terminal 51b for transmitter substrate 51 and a part of copper foil 26 positioned at a side opposite to cathode 25, are carried out by solders 53a and 53b, respectively, each having a length of about several millimeters (a first embodiment).

In ultrasonic transducer 1, the inside of housing 4 is formed as a water-proof structure which can completely prevent water from entering into transmitter/receiver circuit substrate assembly 5 or connection portions, by forming a resin mold 8 after attaching the transmitter/receiver circuit substrate assembly 5 and completing the above-described electrical connection. The resin mold 8 is formed, for example, by injecting/charging of urethane resin, epoxy resin, silicone resin, etc. In particular, because silicone resin has a water repellency, it is very effective as water-proof means. Where, by using an opaque silicone resin, it can also be achieved to protect the security in transmitter/receiver circuit substrate assembly 5.

Figure 3:
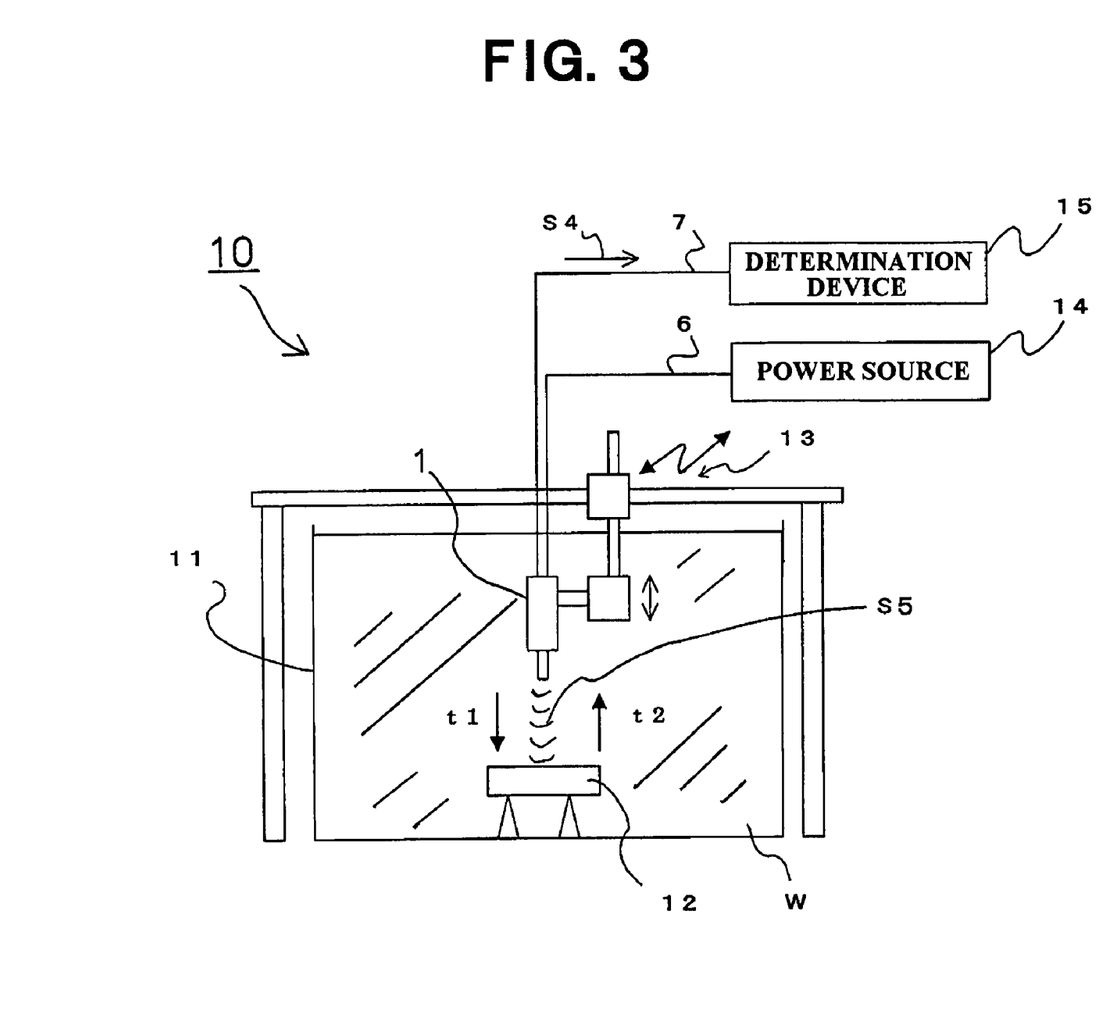
FIG. 3 is a schematic diagram showing an example of an ultrasonic inspection apparatus incorporating an ultrasonic transducer according to the present invention.

Ultrasonic transducer 1 thus constructed is incorporated into and used for an ultrasonic inspection apparatus 10 shown in FIG. 3. FIG. 3 shows a schematic structure of the ultrasonic inspection apparatus incorporating the ultrasonic transducer according to the present invention, FIG. 4 depicts a block diagram showing the function of the ultrasonic inspection apparatus incorporating the ultrasonic transducer according to the present invention, and FIG. 5 depicts a time chart showing output timings of a trigger signal, a drive pulse and an echo signal in the ultrasonic transducer according to the present invention.

Figure 4:
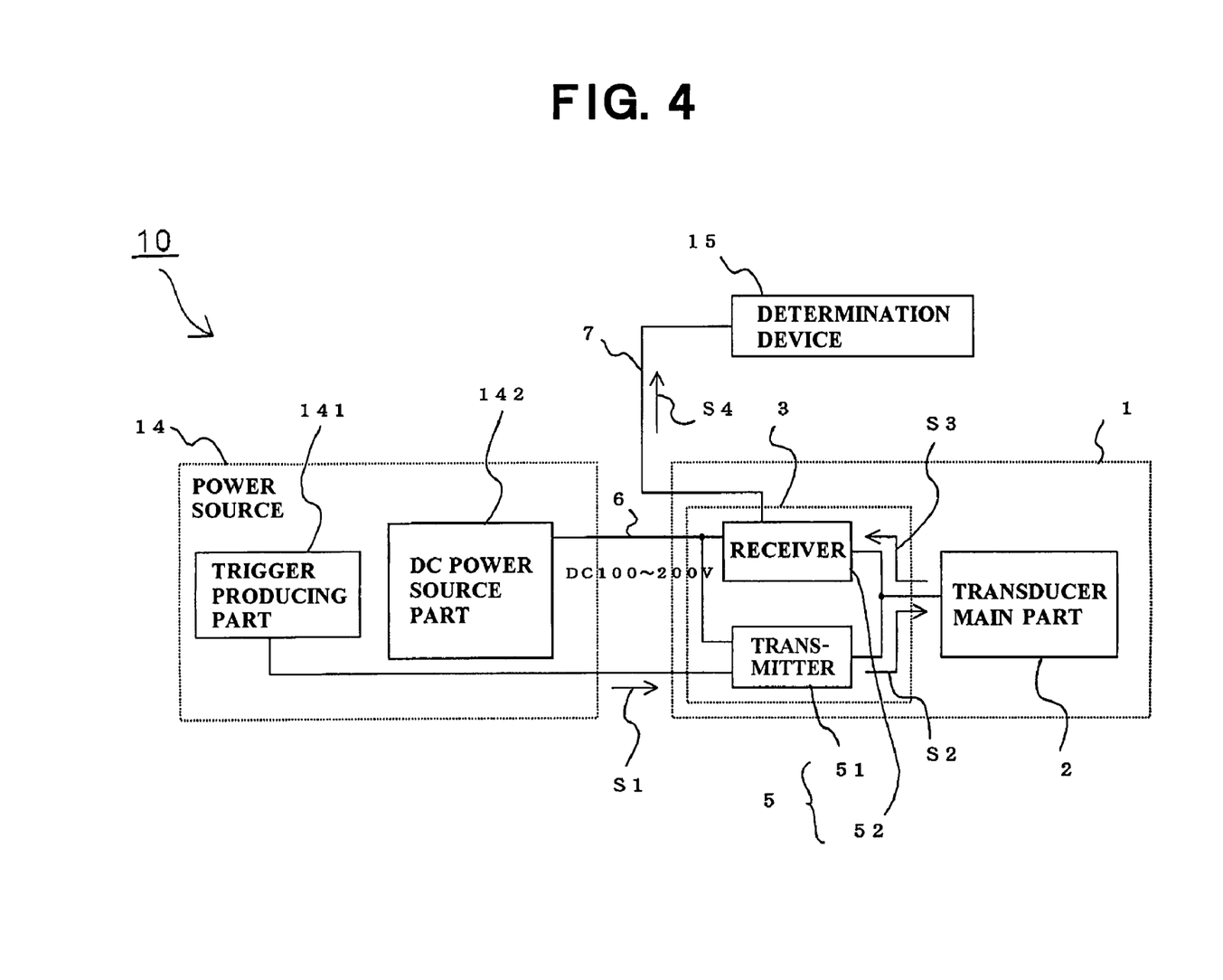
FIG. 4 is a block diagram showing a function of an ultrasonic inspection apparatus incorporating an ultrasonic transducer according to the present invention.

In FIGS. 3 and 4, ultrasonic inspection apparatus 10 comprises water bath 11 filled with water W, sample to be examined 12 provided to be dipped in water bath 11, ultrasonic transducer 1 according to the present invention, scanning device 13 for moving the ultrasonic transducer 1 in horizontal and vertical directions, power source 14 for producing trigger signal S1 and supplying a DC power to transmitter/receiver circuit substrate assembly 5, and determination device 15 for determining existence of defect in the sample 12 based on the RF signal S4 outputted from the ultrasonic transducer 1. Where, in power source 14, more concretely, a trigger producing part 141 produces trigger signal S1, and a DC power source part 142 supplies a DC power, for example, in a range of DC 100-200 V.

Next, the operation of ultrasonic inspection apparatus 10 will be explained. Trigger producing part 141 sends trigger signal S1 to transmitter substrate 51. Transmitter substrate 51 produces drive pulse S2 at a timing decided by trigger signal S1, and sends it to transducer main part 2. By this drive pulse S2, oscillator 24 emits ultrasonic wave S5 having a frequency component decided by the electrical and mechanical design of transducer main part 2. The frequency of this ultrasonic wave S5 is set, for example, at a value in a range of about 10 MHz to about 200 MHz. In this embodiment, because the frequency band of a used sensor is from 20 MHz to 80 MHz, 90 MHz is set as the upper limit of the frequency. Of course, it is possible to set the upper limit at a value more than 200 MHz. As shown in FIG. 3, ultrasonic wave S5 emitted from oscillator 24 is propagated in water, and after time t1, it reaches the surface of sample to be examined 12. Then, the ultrasonic wave S5 is reflected at the surface of the sample 12, and after time t2, it returns to oscillator 24 and vibrates the oscillator 24.

The vibration of oscillator 24 is transformed into an electric signal, and it is taken into transmitter substrate 51 as echo signal S3 and then taken into receiver substrate 52 via connector 58. In receiver substrate 52, the echo signal S3 is amplified by an incorporated amplifying circuit and the amplified signal is sent to determination device 15 as RF signal S4. In determination device 15, existence of defect in sample 12 is determined based on the wave form of this RF signal S4. The determination of existence of defect is carried out, for example, by comparison treatment between a master signal stored in determination device 15 beforehand and the RF signal S4 sent from receiver substrate 52. Where, the master signal means an RF signal obtained from a sample having no defect. Scanning device 13 moves ultrasonic transducer 1 in the horizontal direction, the above-described operation is repeated, and the existence of defect is determined over the entire area of the sample 12.

In ultrasonic transducer 1 according to this embodiment, the electrical connection between signal input/output terminal 51a for transmitter substrate 51 and anode 21 in transducer main part 2, and the electrical connection between signal input/output terminal 51b for transmitter substrate 51 and a part of copper foil 26 positioned at the side opposite to cathode 25, are carried out by solders 53a and 53b, respectively. Each of the lengths of solders 53a and 53b is about several millimeters. This length is set based on a length of 100/fmax [cm] according to the present invention. Where, fmax is a maximum operational frequency [MHz] of ultrasonic wave S5 emitted from oscillator 24, and in this embodiment, it is 90 MHz. Therefore, the upper limit of the length of solder 53a, 53b becomes 100/90=1.1 [cm]. Because the length of the connecting means is set at a length of the upper limit adequately determined in accordance with the maximum operational frequency or less, when drive pulse S2 is sent from signal input/output terminal 51a, 51b to transducer main part 2, the drive pulse S2 is suppressed to be attenuated and weakened. Similarly, when echo signal S3 is sent from transducer main part 2 to signal input/output terminal 51a, 51b, the echo signal is suppressed to be attenuated and weakened. As a result, even in a case of a small sample to be examined 12, a desirable defect examination can be achieved at an excellent examination accuracy.

Figure 6:
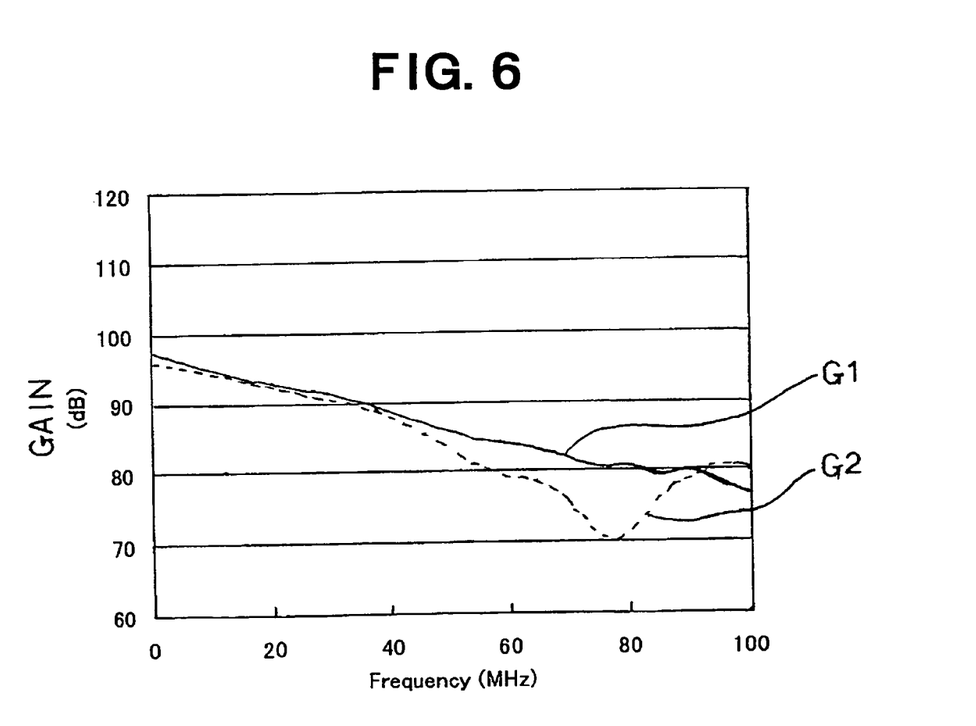
FIG. 6 is a graph showing comparison in frequency property between a case using an ultrasonic transducer according to the present invention and a case using a conventional ultrasonic transducer.

Such an excellent effect according to the present invention is shown in FIG. 6 more concretely. FIG. 6 shows the comparison in frequency property between a case using the ultrasonic transducer according to the present invention and a case using a conventional ultrasonic transducer such as one shown in FIG. 12. In FIG. 6, the solid line G1 shows a frequency property of the case using the ultrasonic transducer 1 according to the present invention, and the dotted line G2 shows a frequency property of the case using the conventional ultrasonic transducer 50. The solid line G1 is higher in gain than the dotted line G2 in the range of 90 MHz or less, and this represents an advantage according to the present invention. Where, the length of lead wire 17 used for the electrical connection between the conventional ultrasonic transducer 50 and the transmitter/receiver circuit 16 was set at 1 m.

Figure 7:
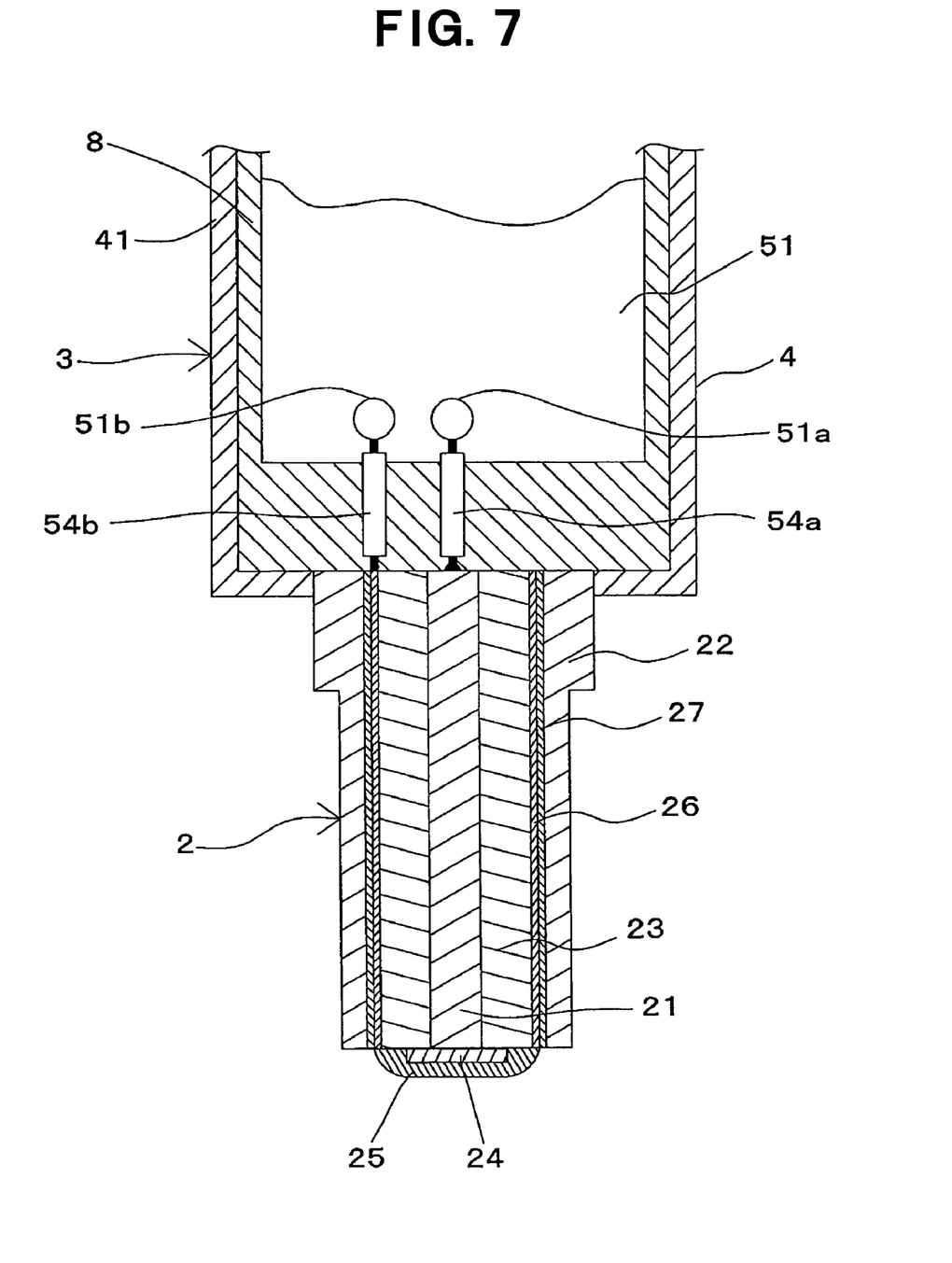
FIG. 7 is a sectional view of a part of an ultrasonic transducer according to a second embodiment of the present invention.

In the above-described embodiment, although solders 53a and 53b are employed for the electrical connection between signal input/output terminal 51a for transmitter substrate 51 and anode 21 in transducer main part 2 and the electrical connection between signal input/output terminal 51b for transmitter substrate 51 and a part of copper foil 26 positioned at the side opposite to cathode 25, instead of solders 53a and 53b, as shown in FIG. 7, lead wires 54a and 54b each having a length of 1.1 [cm] or less may be employed (a second embodiment). Even in this case, an advantage similar to that in the above-described first embodiment can be expected. Where, as the electrically connecting means, instead of solders 53a and 53b and lead wires 54a and 54b, for example, means by thermocompression bonding, conductive paste or sputtering.

Figure 8:
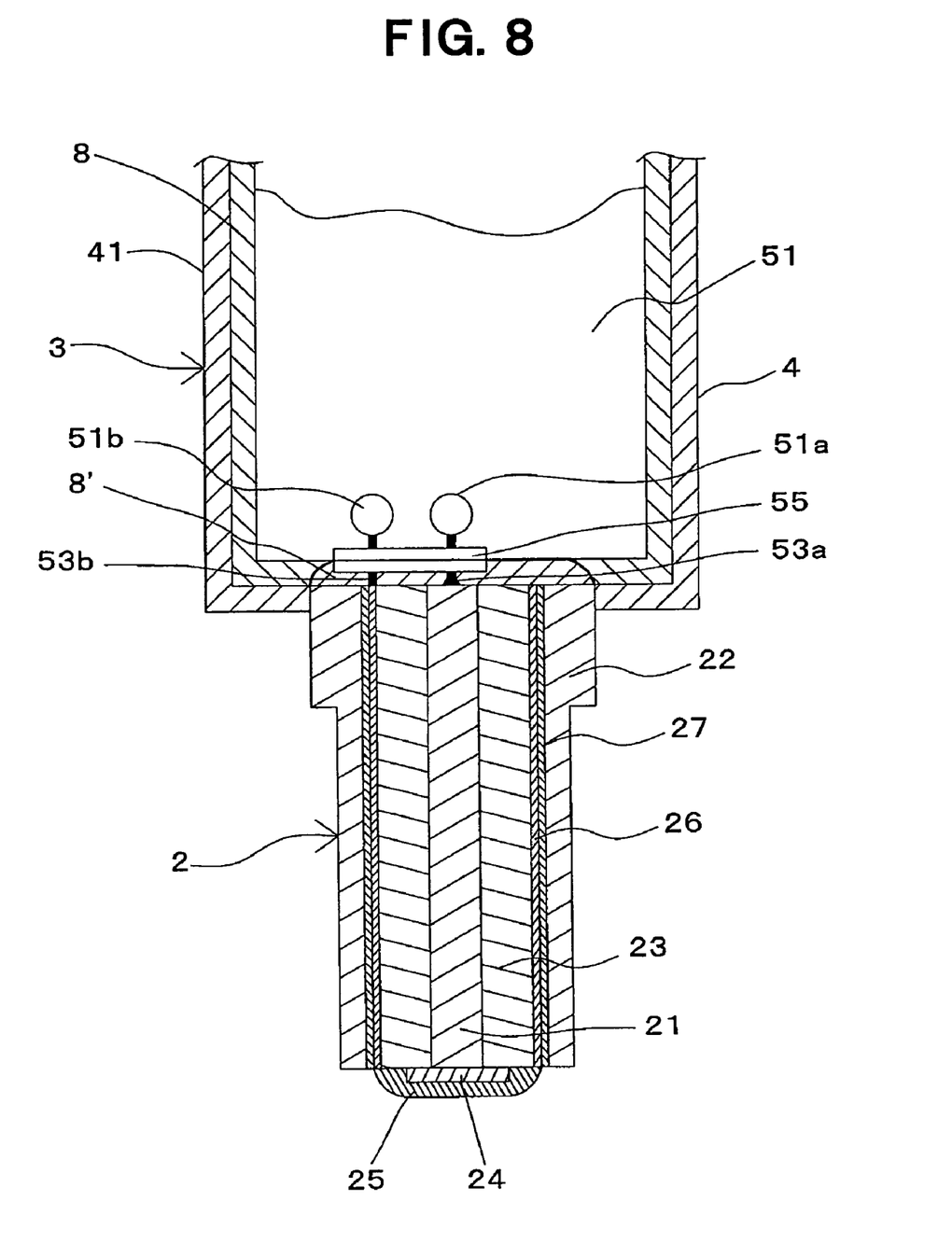
FIG. 8 is a sectional view of a part of an ultrasonic transducer according to a third embodiment of the present invention.
Figure 9:
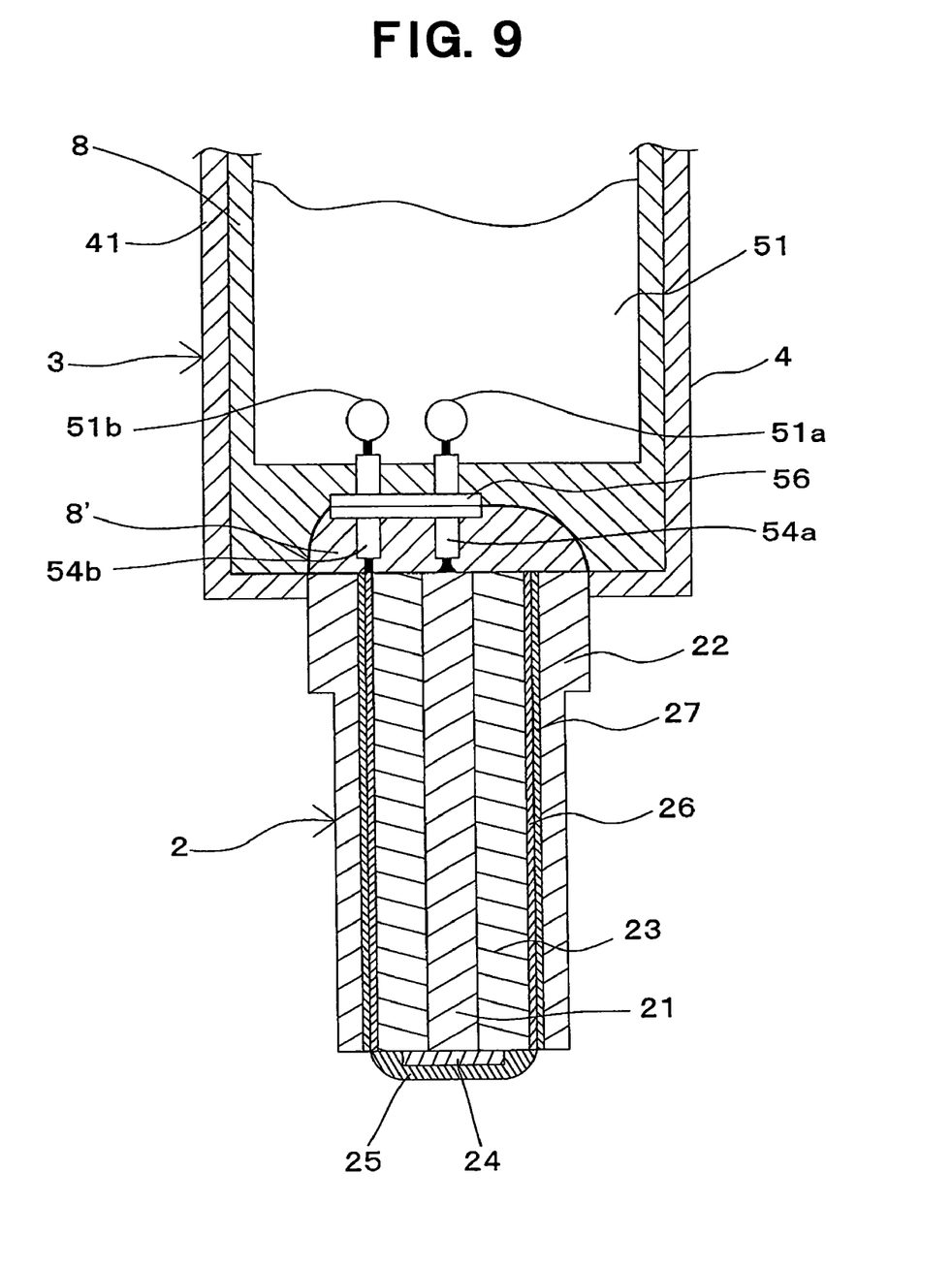
FIG. 9 is a sectional view of a part of an ultrasonic transducer according to a fourth embodiment of the present invention.

Further, as shown in FIG. 8, connector 55 may be interposed at respective intermediate positions of solders 53a and 53b (a third embodiment). Similarly, as shown in FIG. 9, connector 55 may be interposed at respective intermediate positions of lead wires 54a and 54b (a fourth embodiment). In these cases, it is preferred that another resin mold 8' capable of being separated from resin mold 8 is formed around connector 55, 56 at the side of transducer main part 2.

Further, in the present invention, because transmitter substrate 51 and receiver substrate 52 are provided in housing 4 so as to confront each other, the housing 4 can be made small. Furthermore, because transmitter substrate 51 and receiver substrate 52 are connected to each other by connector 58 at a condition free to be attached and detached, by using connector 55 or 56 as shown in the third and fourth embodiments, it is possible to separate transmitter substrate 51 and receiver substrate 52 as respective individual parts. Therefore, an excellent maintenance property can be realized, and an additional function may be easily added particularly in a technology development stage as needed.

Figure 10:
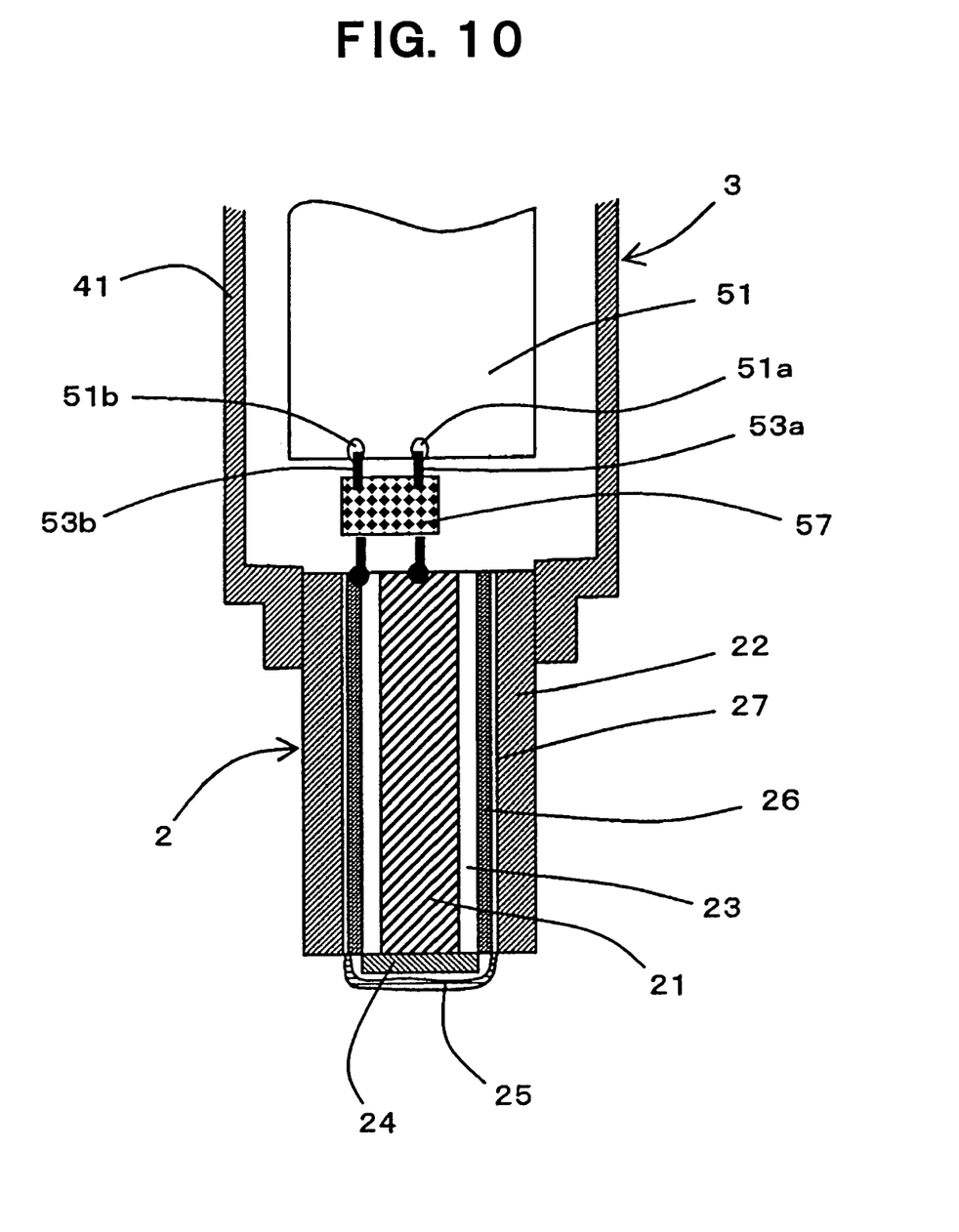
FIG. 10 is a sectional view of a part of an ultrasonic transducer according to a fifth embodiment of the present invention.

Further, in the present invention, as shown in FIG. 10 as a fifth embodiment, the electrical connection between signal input/output terminals 51a, 51b and oscillator 24 may be carried out via a matched circuit substrate 57. By using such a matched circuit substrate 57, electric signals between signal input/output terminals 51a, 51b and oscillator 24 may be well matched for exhibiting the desirable function of ultrasonic transducer 1.

Figure 11:
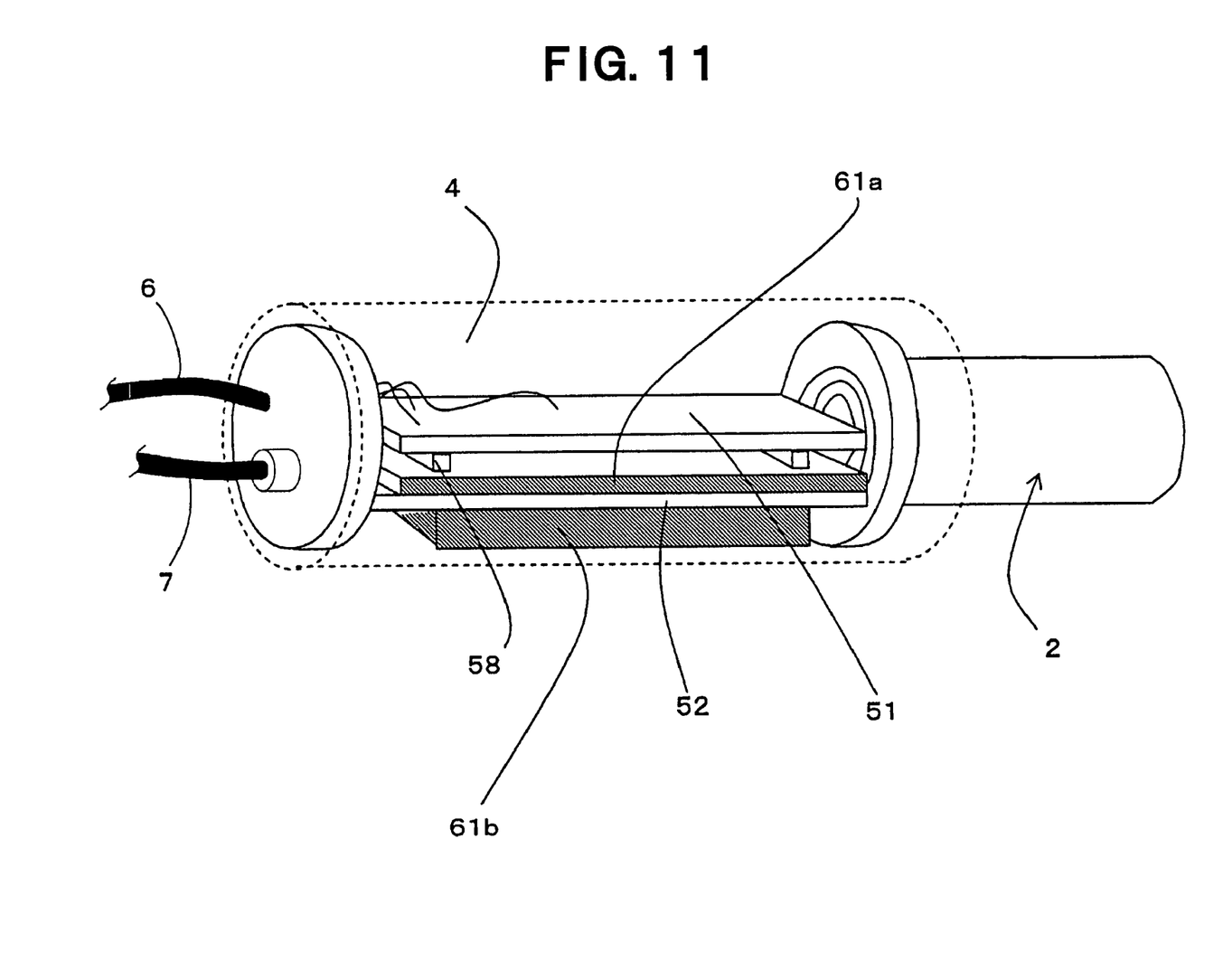
FIG. 11 is a schematic perspective view of an ultrasonic transducer according to a sixth embodiment of the present invention.

Furthermore, because transmitter substrate 51 and receiver substrate 52 are disposed in housing 4 at a relatively close condition, there may be a fear that the receiver substrate 52 is affected by the electromagnetic wave from the transmitter substrate 51 and the affection becomes a noise in the receiver substrate 52. In order to prevent such an affection, it is preferred that an electromagnetic wave shielding means is interposed between transmitter substrate 51 and receiver substrate 52. Concretely, as shown in FIG. 11 as a sixth embodiment of the present invention, a shield case 61a is preferably interposed between transmitter substrate 51 and receiver substrate 52, and more preferably, a shield case 61b is provided at the outer surface side of the receiver substrate 52, so that the receiver substrate 52 can be covered with shield cases 61a and 61b. Each of these shield cases 61a and 61b is preferably made from a shield material formed by covering an iron base material with another metal layer having a high surface conductivity such as a plating layer of tin. By shield cases 61a and 61b thus constructed, electric wave and magnetic wave forming an electromagnetic wave can be both shielded. Because the electromagnetic wave is shielded for receiver substrate 52, the signal grant may be reinforced.

Although embodiments of the present invention have been described in detail herein, the scope of the invention is not limited thereto. It will be appreciated by those skilled in the art that various modifications may be made without departing from the scope of the invention. Accordingly, the embodiments disclosed herein are only exemplary. It is to be understood that the scope of the invention is not to be limited thereby, but is to be determined by the claims which follow.

This application is based on Japanese Patent Application No. 2007-019872, filed on Jan. 30, 2007, the contents of which are incorporated hereinto by reference.

What is claimed is:

1. An ultrasonic transducer incorporated into and used for an ultrasonic inspection apparatus, which projects an ultrasonic wave to a sample to be examined, dipped in water, through the water, receives a reflected wave from said sample and detects a defect such as a break away or a flaw in said sample based on a wave form of an echo signal of said reflected wave, said ultrasonic transducer comprising:

a transducer main part having an oscillator which emits said ultrasonic wave in accordance with a drive pulse, receives said reflected wave from said sample and outputs the received reflected wave as said echo signal;

a transmitter substrate provided for producing said drive pulse which gives an energy for emitting said ultrasonic wave to said oscillator in said transducer main part;

a receiver substrate provided for amplifying said echo signal received by said oscillator in said transducer main part;

a housing formed as a cylindrical shape for containing a transmitter/receiver circuit substrate assembly which is formed by electrically connecting said transmitter substrate and said receiver substrate at a form confronted with each other and at a condition free to be attached and detached; and connecting member for electrically connecting between a signal input/output terminal, provided on said transmitter substrate and functioning as an output terminal for outputting said drive pulse to said oscillator as well as functioning as an input terminal for inputting said echo signal outputted from said oscillator, and said oscillator in said transducer main part, wherein, when a maximum operational frequency of said ultrasonic wave emitted from said oscillator is referred to as fmax [MHz], said connecting member is set at a length of 100/fmax [cm] or less.

2. The ultrasonic transducer according to claim 1, wherein said transducer main part and said transmitter/receiver circuit substrate assembly are integrated with each other.

3. The ultrasonic transducer according to claim 1, wherein said signal input/output terminal and said oscillator are electrically connected via a solder.

4. The ultrasonic transducer according to claim 1, wherein said signal input/output terminal and said oscillator are electrically connected via a lead wire.

5. The ultrasonic transducer according to claim 1, wherein said signal input/output terminal and said oscillator are electrically connected via a connector which is free to be connected and disconnected.

6. The ultrasonic transducer according to claim 1, wherein said signal input/output terminal and said oscillator are electrically connected via a matched circuit substrate.

7. The ultrasonic transducer according to claim 1, wherein an electromagnetic wave shielding member is interposed between said transmitter substrate and said receiver substrate.

* * * * *